United States Patent
Yahata (10) Patent No.: US 9,176,106 B2
(45) Date of Patent: Nov. 3, 2015

(54) TOTAL ORGANIC CARBON METER PROVIDED WITH SYSTEM BLANK FUNCTION

(71) Applicant: SHIMADZU CORPORATION, Kyoto-shi, Kyoto (JP)

(72) Inventor: Masahito Yahata, Shiga (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/041,488

(22) Filed: Sep. 30, 2013

(65) Prior Publication Data

US 2014/0030814 A1 Jan. 30, 2014

Related U.S. Application Data

(62) Division of application No. 13/266,005, filed as application No. PCT/JP2009/058122 on Apr. 24, 2009, now abandoned.

(51) Int. Cl.
  *G01N 33/18* (2006.01)
  *G01N 27/06* (2006.01)

(52) U.S. Cl.
  CPC ............ *G01N 33/1846* (2013.01); *G01N 27/06* (2013.01); *Y10T 436/235* (2015.01)

(58) Field of Classification Search
  USPC ........................................................ 436/146
  See application file for complete search history.

(56) References Cited

U.S. PATENT DOCUMENTS 5,443,991 A * 8/1995 Godec et al. .................. 436/145
6,228,325 B1 5/2001 Godec et al.
(Continued)

FOREIGN PATENT DOCUMENTS

EP 0150923 A2 8/1985
JP 56-163452 A 12/1981
(Continued)

OTHER PUBLICATIONS

International Search Report of PCT/JP2009/058122, mailing date Aug. 4, 2009.
(Continued)

*Primary Examiner* — Jill Warden
*Assistant Examiner* — Julie Tavares
(74) *Attorney, Agent, or Firm* — Westerman, Hattori, Daniels & Adrian, LLP (57) ABSTRACT

A total organic carbon measuring device comprises: a sample supply unit that collects and supplies sample water; an oxidative decomposition unit that is connected to the sample supply unit and oxidizes organic matter contained in the sample water supplied from the sample supply unit to carbon dioxide; a carbon dioxide separation unit that transfers carbon dioxide from the sample water that has passed through the oxidative decomposition unit to measurement water consisting of deionized water; a conductivity measuring unit that measures the conductivity of the measurement water flowing from the carbon dioxide separation unit; and an arithmetic processing unit that calculates the TOC concentration of the sample water from a measured value obtained by the conductivity measuring unit. A measured value obtained by the conductivity measuring unit when pure water subjected to aeration treatment is allowed to pass through the oxidative decomposition unit of which oxidative decomposition function is turned off and then flows through a sample water channel is defined as a system blank value.

2 Claims, 6 Drawing Sheets

(56) References Cited

U.S. PATENT DOCUMENTS

| | | | |
|---|---|---|---|
| 6,447,725 B1 * | 9/2002 | Inoue et al. | 422/80 |
| 6,734,021 B1 | 5/2004 | Saito et al. | |
| 2007/0254374 A1 * | 11/2007 | Iharada et al. | 436/146 |
| 2008/0045771 A1 | 2/2008 | Regla | |
| 2008/0220533 A1 | 9/2008 | Fujiyama et al. | |
| 2009/0074619 A1 * | 3/2009 | Akechi et al. | 422/69 |
| 2010/0098588 A1 | 4/2010 | Fujiyama et al. | |

FOREIGN PATENT DOCUMENTS

| | | |
|---|---|---|
| JP | 5-188051 A | 7/1993 |
| JP | 2001-149930 A | 6/2001 |
| JP | 2001-318089 A | 11/2001 |
| JP | 2006-300633 A | 11/2006 |
| JP | 2007-040729 A | 2/2007 |
| JP | 2007-093209 A | 4/2007 |
| JP | 2008-180662 A | 8/2008 |
| WO | 91/13362 A1 | 9/1991 |
| WO | 2006/126296 A1 | 11/2006 |
| WO | WO 2007129383 A1 * | 11/2007 |
| WO | 2008/047405 A1 | 4/2008 |

OTHER PUBLICATIONS

Extended European Search Report dated Feb. 23, 2015, issued in corresponding European Patent Application No. 09843655.3 (7 pages).

* cited by examiner

TOTAL ORGANIC CARBON METER PROVIDED WITH SYSTEM BLANK FUNCTION

CROSS REFERENCE TO RELATED APPLICATIONS

This is a divisional of U.S. application Ser. No. 13/266,005 filed on Oct. 24, 2011, which is a 371 of PCT/JP2009/058122 filed on Apr. 24, 2009, the entire contents of which is incorporated herein by reference.

BACKGROUND OF THE INVENTION

1. Field of the Invention

The present invention relates to a total organic carbon measuring device (also referred to as a "TOC meter") for measuring the total organic carbon (TOC) content, total carbon (TC) content, or inorganic carbon (IC) content of sample water, for example, a total organic carbon measuring device in which organic matter is separated from water containing few impurities, called pure water or ultrapure water, by a carbon dioxide separation unit to assay the TOC concentration of the water based on conductivity.

2. Description of the Related Art

For the purpose of management of water containing few impurities, such as water for manufacturing drugs, process water for semiconductor manufacturing, cooling water, boiler water, or tap water, the organic matter (TOC) content of a sample of such water is measured.

As a TOC measuring device, a TOC meter comprising a total carbon combustion unit using an oxidation catalyst is widely used. The TOC meter measures TOC by converting TOC contained in sample water to $CO_2$ gas and measuring the $CO_2$ concentration in the gas phase by a nondispersive infrared analyzer.

On the other hand, a device that measures the TOC concentration of sample water while keeping the sample water in the liquid phase has also been developed. In the case of such a device that measures sample water while keeping it in the liquid phase, organic matter contained in sample water is converted to carbon dioxide by an oxidation reactor. The sample water is kept in the liquid phase and is allowed to flow through a sample water channel. The sample water channel is in contact with a measurement water channel, through which measurement water flows, with a gas permeable membrane being interposed therebetween, and therefore carbon dioxide contained in the sample water is transferred to measurement water. The measurement water containing carbon dioxide transferred from the sample water is sent to a conductivity meter to measure the conductivity thereof. The carbon dioxide concentration of the sample water can be determined from the measured conductivity of the measurement water, and a previously-prepared calibration curve representing the relationship between the conductivity of measurement water and the carbon dioxide concentration of sample water (see Patent Document 1).

The present invention is directed to such a device that measures the TOC concentration of sample water while keeping the sample water in the liquid phase.

In the measurement of TOC, a measuring device needs to have a blank value of its own, that is, a system blank value. The system blank value of a TOC meter is a signal obtained by measuring, as a sample, pure water whose organic carbon content is infinitely close to zero, and is used as a reference for measurement by the TOC meter. Such a system blank value is essential to quantitative measurement of very low TOC levels of pure water and the like.

In pure water that is in contact with air, $CO_2$ contained in air is dissolved. Therefore, it is difficult to obtain pure water whose carbon content is infinitely close to zero when the pure water is exposed to the atmosphere. In the case of a conventional TOC meter that comprises a total carbon combustion unit using an oxidation catalyst and measures TOC by converting TOC contained in sample water to $CO_2$ gas and measuring the $CO_2$ concentration in the gas phase, pure water is vaporized while TOC contained in the pure water is decomposed to $CO_2$ gas by oxidation and removed, and then remaining water vapor is condensed to recover the pure water. The cycle of vaporization, oxidative decomposition, and recovery is repeated in this device to obtain pure water whose organic carbon content is infinitely close to zero. The conventional TOC meter uses the measured value of the thus obtained pure water as a system blank value. Patent Document 1: WO2008/047405

The present invention is directed to a TOC measuring device that is not provided with, as a channel for measurement, a channel for performing vaporization and oxidative decomposition of sample water at the same time and then condensing the remaining water vapor. In order to provide a channel for preparing blank water used to obtain a system blank value, it is necessary to provide not only a channel different from a channel for measurement but also a container intended for exclusive use as a pure water trap. Even when such a channel for preparing blank water is provided, it takes a long time to obtain pure water whose organic carbon content is infinitely close to zero by repeated cycles of vaporization and oxidative decomposition of sample water and condensation of water vapor.

SUMMARY OF THE INVENTION

It is therefore an object of the present invention to provide a device that measures the TOC concentration of sample water while keeping the sample water in the liquid phase and is capable of easily obtaining a system blank value.

The present invention is directed to a TOC meter comprising: a sample supply unit that collects and supplies sample water; an oxidative decomposition unit that is connected to the sample supply unit and oxidizes organic matter contained in the sample water supplied from the sample supply unit to carbon dioxide; a carbon dioxide separation unit that transfers carbon dioxide contained in the sample water that has passed through the oxidative decomposition unit to measurement water consisting of deionized water; a conductivity measuring unit that measures the conductivity of the measurement water flowing from the carbon dioxide separation unit; and an arithmetic processing unit that calculates the TOC concentration of the sample water from a measured value obtained by the conductivity measuring unit.

The sample supply unit has a system for subjecting the collected sample water to aeration treatment using a gas containing no carbon dioxide.

The oxidative decomposition unit has oxidative decomposition function that oxidizes organic matter contained in the supplied sample water to carbon dioxide and is capable of turning on and off the oxidative decomposition function.

The carbon dioxide separation unit includes: a sample water channel through which the sample water that has passed through the oxidative decomposition unit flows; a measurement water channel through which measurement water consisting of deionized water flows; and a gas permeable membrane interposed between the sample water channel and the measurement water channel to allow carbon dioxide to be transferred therethrough.

The arithmetic processing unit includes: a system blank holding section that holds, as a system blank value, a measured value obtained by the conductivity measuring unit when pure water collected in the sample supply unit and subjected to aeration treatment is allowed to pass through the oxidative decomposition unit of which oxidative decomposition function is turned off and then flows through the sample water channel; and an arithmetic section that calculates the total organic carbon concentration of sample water from a system blank value held in the system blank holding section and a measured value obtained by the conductivity measuring unit when the sample water is allowed to pass through the oxidative decomposition unit of which oxidative decomposition function is turned on and then flows through the sample water channel.

In the case of a conventional TOC meter that measures TOC by oxidative decomposition of TOC to gas-phase $CO_2$ gas, it is necessary to repeat the cycle of vaporization and oxidative decomposition of pure water and recovery of water vapor into a pure water trap by cooling many times to obtain pure water whose organic carbon content is infinitely close to zero. During this operation, TOC contained in pure water is decomposed to $CO_2$ (inorganic carbon) by oxidation, vaporized into a gas, and discharged to the outside of the system together with a carrier gas. However, gas-liquid equilibrium is established between gasified $CO_2$ and recovered pure water, and part of the gasified $CO_2$ is dissolved in the pure water. In this case, however, the empty space of the pure water trap containing the recovered pure water is aerated by a carrier gas containing little $CO_2$ such as high-purity air so that part of the dissolved $CO_2$ is distributed to the carrier gas. In this way, TOC contained in pure water is converted to $CO_2$ and removed by repeated cycles of vaporization and oxidative decomposition of pure water and recovery, and finally, pure water containing dissolved $CO_2$ (inorganic carbon) whose concentration depends on the partial pressure of $CO_2$ in a carrier gas is recovered. The measured intensity of the obtained pure water is conventionally used as a system blank value. That is, the obtained system blank value is equivalent to the measured intensity of $CO_2$ (inorganic carbon) remaining in pure water subjected to aeration treatment using a carrier gas until $CO_2$ is removed.

When the $CO_2$ concentration of a carrier gas is zero, $CO_2$ contained in recovered pure water is eventually completely removed by repeated cycles of vaporization, oxidative decomposition, and recovery. However, even when high-purity air is used as a carrier gas, it contains $CO_2$ or hydrocarbons although its amount is as small as less than 1 ppm, and therefore, a system blank intensity has a certain value.

In the case of the TOC meter according to the present invention, only $CO_2$ transferred from sample water to measurement water through the gas permeable membrane in the carbon dioxide separation unit is detected by the conductivity measuring unit. When pure water is collected as sample water in the sample supply unit and subjected to aeration treatment using a gas containing no $CO_2$, $CO_2$ (inorganic carbon) contained in the sample water is removed and only ionized TOC remains in the sample water. Even when remaining in the sample water, the TOC is kept in its ionic state when the oxidative decomposition function of the oxidative decomposition unit is turned off, and therefore, the TOC is not transferred to measurement water through the gas permeable membrane in the carbon dioxide separation unit. Therefore, the pure water flowing through the sample water channel is equivalent to one containing no $CO_2$ gas component.

The oxidative decomposition unit may include: an organic matter oxidation part made of a UV-permeable material comprising a channel through which sample water flows; and an ultraviolet light source that irradiates sample water with ultraviolet light from the outside of the organic matter oxidation part. In this case, the oxidative decomposition function of the oxidative decomposition unit is turned on and off by the ultraviolet light source.

Alternatively, the oxidative decomposition unit may include an organic matter oxidation part made of a UV-permeable material comprising a channel through which sample water flows, an ultraviolet light source that irradiates sample water with ultraviolet light from the outside of the organic matter oxidation part, and a shutter interposed between the organic matter oxidation part and the ultraviolet light source. In this case, the oxidative decomposition function of the oxidative decomposition unit is turned on and off by opening and closing the shutter.

The arithmetic section of the arithmetic processing unit may hold calibration curve data representing the relationship between a measured value obtained by the conductivity measuring unit and the total organic carbon concentration of sample water supplied from the sample supply unit. In this case, the arithmetic processing unit corrects the calibration curve data using a system blank value held in the system blank holding section to obtain corrected calibration curve data, and calculates the total organic carbon concentration of sample water from the corrected calibration curve data and a measured value obtained by the conductivity measuring unit when the sample water is measured.

The corrected calibration curve data may be obtained by, for example, shifting the calibration curve data obtained from a measured value so that its intercept value becomes a system blank value held in the system blank holding section.

The sample supply unit may include a multi-port valve having at least a port connected to a channel for supplying sample water, a port connected to a channel for supplying pure water, a port connected to the oxidative decomposition unit, a port opened to the atmosphere, and a common port connected to any one of the ports by switching, a syringe that is connected to the common port of the multi-port valve and collects and sends sample water by slidably moving a piston in a cylinder in a vertical direction, and a gas supply channel that is connected to the lower end portion of the cylinder of the syringe at a position above the piston in a state where the piston is located at the lower end of the cylinder to supply a gas containing no carbon dioxide into the cylinder.

In order to remove a $CO_2$ gas component contained in sample water by subjecting the sample water to aeration treatment, the sample water is preferably acidified. Therefore, it is preferred that the multi-port valve further has another port connected to an acid supply channel for supplying an acid for acidifying sample water collected in the syringe.

According to the present invention, commercially-available pure water is subjected to aeration treatment using a gas containing no carbon dioxide such as high-purity air and is measured in a state where the oxidative decomposition function of the oxidative decomposition unit is turned off, which makes it possible to obtain a system blank value without preparing pure water containing no organic carbon by repeated cycles of vaporization, oxidative decomposition, and recovery. As compared to a conventional method by which only a small amount of pure water containing no organic carbon can be obtained despite its complicated operation, a method according to the present invention makes it possible to easily perform measurement any time and any number of times.

DESCRIPTION OF THE REFERENCE NUMERALS

2: sample water channel
4: intermediate water channel
6: measurement water channel
8, 10: gas permeable membranes
20, 40: carbon dioxide separation units
24: organic matter oxidation part
26: ultraviolet lamp
27: shutter
34: conductivity meter
102: sample supply unit
104: channel switching valve
106: syringe
118: oxidative decomposition unit
120: gas supply channel
124: carbon dioxide separation unit
128: arithmetic processing unit
130: system blank holding section
132: arithmetic section

DETAILED DESCRIPTION OF THE INVENTION

Figure 1:
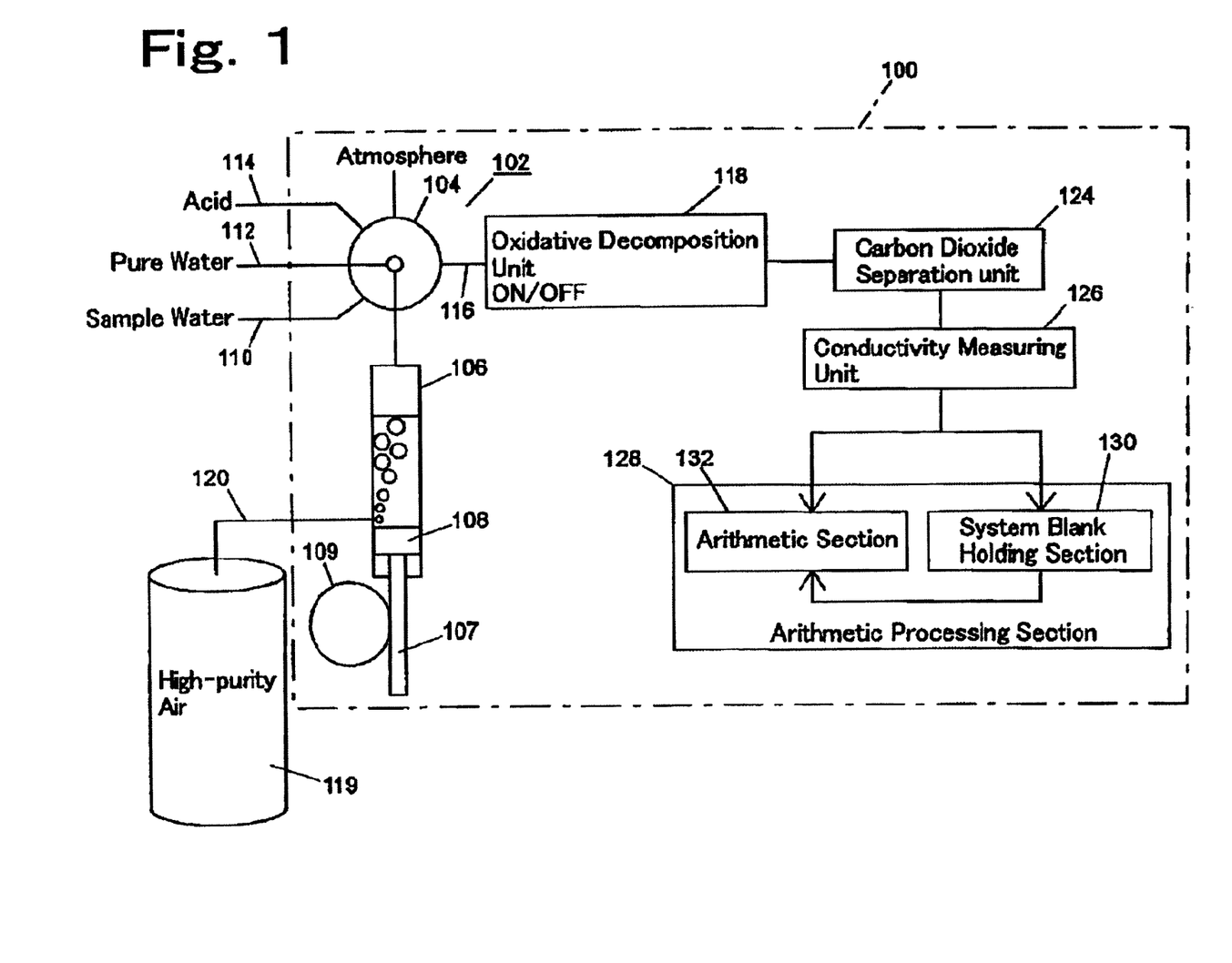
FIG. 1 is a block diagram schematically showing one embodiment of the present invention.

FIG. 1 is a schematic view of a TOC meter according to one embodiment of the present invention. It is to be noted that in FIG. 1, components surrounded by a dashed-line box are housed in a housing of a TOC meter 100 and the area outside the dashed-line box represents the outside of the housing.

In the TOC meter 100, a sample supply unit 102 is provided. The sample supply unit 102 includes a channel switching valve 104 constituted from a multi-port valve such as a 6—port valve or an 8—port valve, a water sampling syringe 106 connected to a common port of the valve 104, and a gas supply channel 120 through which a gas containing no carbon dioxide is supplied into the cylinder 106.

A channel 110 is connected to one of the ports of the valve 104 to receive sample water from the outside of the housing of the TOC meter. A channel 112 is connected to another one of the ports of the valve 104 to receive pure water from the outside of the housing. A channel 114 is connected to yet another one of the ports of the valve 104 to receive an acid for acidifying sample water or pure water collected in the syringe 106 from the outside of the housing. A channel 116 connected to an oxidative decomposition unit 118 is connected to yet another one of the ports of the valve 104. Yet another one of the ports of the valve 104 can be opened to the atmosphere.

As the acid, an inorganic acid such as hydrochloric acid, sulfuric acid, or phosphoric acid is used. The pH of sample water or pure water contained in the syringe 106 is preferably adjusted to 4 or less by adding such an acid.

The valve 104 includes a stator having a plurality of ports, and channel switching is performed by rotating a rotor so that the syringe 106 connected to the common port of the valve 104 is connected to any one of the ports.

The syringe 106 includes a cylinder and a piston 108, and sample water or pure water and, in addition, an acid can be introduced into the syringe 106 by slidably moving the piston 108 in a vertical direction while the inside of the cylinder is kept liquid-tight. The sample water or pure water collected in the syringe 106 can be supplied to the oxidative decomposition unit 118 through the valve 104 and the channel 116 by pushing the piston 108 upward. The piston 108 is attached to the tip of a plunger 107. The piston 108 is slidably moved in the cylinder in a vertical direction by driving the plunger 107 by a syringe driving unit 109 driven by a motor.

The gas supply channel 120 is connected to the lower end portion of the cylinder of the syringe 106 to supply a gas containing no carbon dioxide into the syringe 106 for aeration treatment. The position at which the gas supply channel 120 is connected to the cylinder is above the piston 108 in a state where the piston 108 is located at the lower end of the cylinder. Examples of the gas containing no carbon dioxide include, but are not limited to, high-purity air contained in a bomb 119 and high-purity air supplied through a column filled with a filler that absorbs carbon dioxide gas.

When flowing through a channel in an organic matter oxidation part of the oxidative decomposition unit 118, sample water or pure water (hereinafter, when only the term "sample water" is used, it refers to sample water or pure water) is irradiated with ultraviolet light to decompose organic matter contained in the sample water by oxidation to carbon dioxide gas.

The sample water that has passed through the oxidative decomposition unit 118 is introduced into a carbon dioxide separation unit 124. In the carbon dioxide separation unit 124, a carbon dioxide gas component contained in the sample water is transferred to measurement water through a gas permeable membrane. The sample water that has passed through the carbon dioxide separation unit 124 is disposed of.

The measurement water that has passed through the carbon dioxide separation unit 124 is introduced into a conductivity measuring unit 126. The conductivity measuring unit 126 is provided with an electrode, and the measurement water is brought into contact with the electrode to detect the conductivity thereof. The conductivity of the measurement water varies depending on the concentration of the carbon dioxide gas component transferred from the sample water to the measurement water in the carbon dioxide separation unit 124, and therefore, the concentration of the carbon dioxide gas component of the sample water can be determined based on the detected value of conductivity of the measurement water. The carbon dioxide gas component is a component generated by the oxidative decomposition unit 118 through oxidative decomposition of a TOC component contained in the sample water, and therefore, the TOC concentration of the sample water can be determined.

An arithmetic processing unit 128 is connected to the electrode of the conductivity measuring unit 126 for measuring conductivity to calculate the TOC concentration of sample water based on conductivity detected by the conductivity measuring unit 126. The arithmetic processing unit 128 includes a system blank holding section 130 and an arithmetic section 132.

The system blank holding section 130 holds, as a system blank value, a measured value obtained by the conductivity measuring unit 126 when pure water collected in the syringe 106 and subjected to aeration treatment is allowed to pass through the oxidative decomposition unit 118 whose oxidative decomposition function is turned off and then flow through a sample water channel in the carbon dioxide separation unit 118.

The arithmetic section 132 calculates the TOC concentration of sample water from a system blank value held in the system blank holding section 130 and a measured value obtained by the conductivity measuring unit 126 when the sample water is allowed to pass through the oxidative decomposition unit 118 whose oxidative decomposition function is turned on and then flows through the sample water channel in the carbon dioxide separation unit 118.

When a system blank value is measured by the TOC meter, the valve 104 is set so that the channel 112 for receiving pure water is connected to the syringe 106 to collect an appropriate amount of pure water (e.g., 3 mL of pure water) in the syringe 106. Then, the valve 104 is rotated so that the syringe 106 is connected to the port connected to the channel 114 for supplying an acid, and a predetermined amount of acid is suctioned into the syringe 106 by further withdrawing the piston 108 of the syringe 106 to adjust the pH of the pure water to 4 or less. After this, the valve 104 is rotated so that the syringe 106 is connected to the port opened to the atmosphere, and in this state, the piston 108 is withdrawn so as to be located at the lower end of the cylinder. In this state, high-purity air is supplied to the syringe 106 through the channel 120 at a flow rate of, for example, 100 ml/min for 90 seconds to subject the pure water collected in the syringe 106 to aeration treatment so that inorganic carbon is removed from the pure water and released into the atmosphere.

After the completion of the aeration treatment, the valve 104 is rotated so that the syringe 106 is connected to the channel 116 to supply the pure water collected in the syringe 106 to the oxidative decomposition unit 118. At this time, an ultraviolet lamp provided in the oxidative decomposition unit 118 is turned off or a shutter is interposed between an ultraviolet lamp and the oxidative decomposition unit 118, and therefore, even when passing through the oxidative decomposition unit 118, the sample water is not irradiated with ultraviolet light. Therefore, even when remaining in the pure water, an ionized TOC component is not decomposed by oxidation, and the TOC component is sent to the carbon dioxide separation unit 124 while being kept in its ionic state. In the carbon dioxide separation unit 124, the pure water is brought into contact with measurement water with a gas permeable membrane being interposed therebetween. Then, the conductivity of the measurement water is detected by the conductivity measuring unit 126.

As shown in FIG. 1, sample water (or pure water) collected in the syringe 106 is supplied to the oxidative decomposition unit 118 through the channel 116. Hereinbelow, some embodiments of the oxidative decomposition unit 118, the carbon dioxide separation unit 124, and the conductivity measuring unit 126 will be described.

Figure 2:
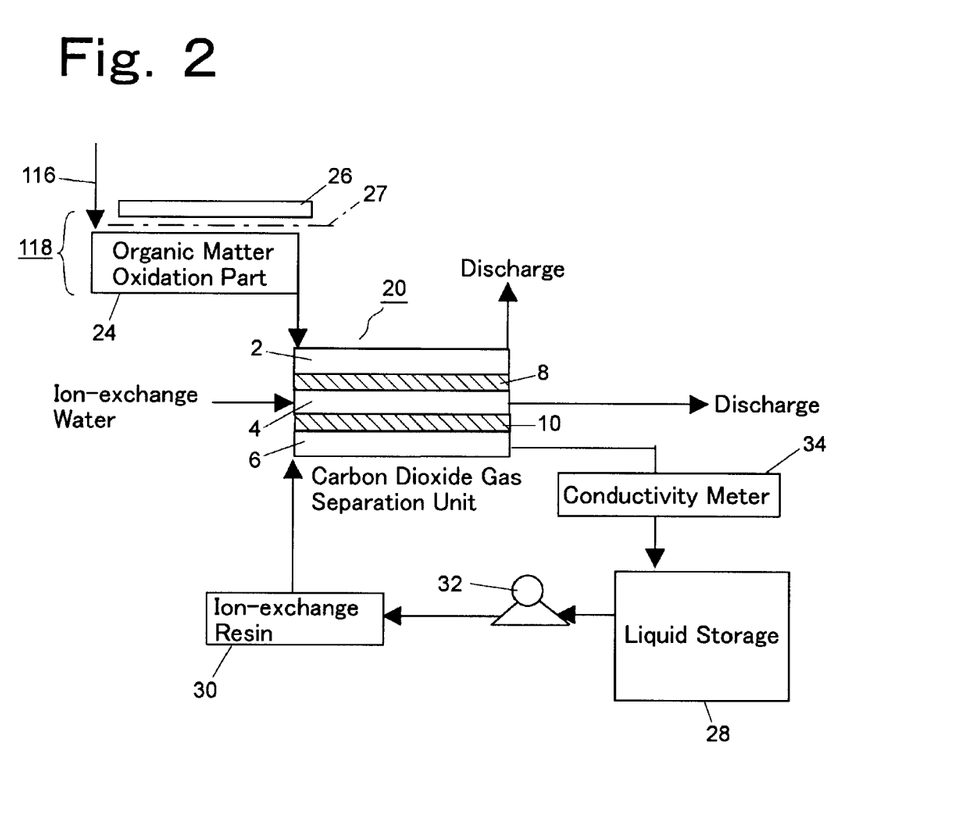
FIG. 2 is a block diagram showing a first embodiment of an oxidative decomposition unit, a carbon dioxide separation unit, and a conductivity measuring unit.

According to an embodiment shown in FIG. 2, the oxidative decomposition unit 118 includes an organic matter oxidation part 24 and an ultraviolet lamp 26. The organic matter oxidation part 24 is made of a UV-permeable material and comprises a channel through which sample water flows. The ultraviolet lamp 26 irradiates sample water with ultraviolet light from the outside of the organic matter oxidation part 24. The organic matter oxidation part 24 is provided with a UV-irradiated portion in which sample water is irradiated with ultraviolet light emitted from the ultraviolet lamp 26. Therefore, organic matter contained in sample water is oxidized to carbon dioxide by UV irradiation while the sample water flows through the UV-irradiated portion. The oxidative decomposition function of the oxidative decomposition unit 118 is turned on and off by the ultraviolet lamp 26.

The oxidative decomposition unit 118 may include a shutter 27 interposed between the organic matter oxidation part 24 and the ultraviolet lamp 26 as shown by a dashed line in FIG. 2. In this case, the oxidative decomposition function of the oxidative decomposition unit 118 can be turned on and off by opening and closing the shutter 27.

Also in the case of other embodiments, the oxidative decomposition unit 118 may have the same structure as that of the embodiment shown in FIG. 2.

The sample water that has passed through the oxidative decomposition unit 118 is supplied to a carbon dioxide separation unit 20 that is one example of the carbon dioxide separation unit 124. The carbon dioxide separation unit 20 includes a sample water channel 2, a measurement water channel 6, and an intermediate water part 4 interposed between the sample water channel 2 and the measurement water channel 6. The sample water channel 2, the intermediate water part 4, and the measurement water channel 6 are stacked in a vertical direction and integrated together. The sample water that has passed through the organic matter oxidation part 24 is allowed to flow through the sample water channel 2. Intermediate water whose pH is in the neutral range and higher than that of the sample water is allowed to flow through or is enclosed in the intermediate water part 4. The intermediate water part 4 is preferably provided as a channel through which the intermediate water flows. Measurement water comprising deionized water is allowed to flow through the measurement water channel 6. The sample water channel 2 and the intermediate water part 4 are in contact with each other with a gas permeable membrane 8 being interposed therebetween, and the intermediate water part 4 and the measurement water channel 6 are also in contact with each other with a gas permeable membrane 10 being interposed therebetween. As the gas permeable membranes 8 and 10, membranes not having carbon dioxide selectivity, such as porous membranes usually used to achieve high-speed measurement, are used.

Ion-exchange water is supplied as deionized water to the measurement water channel 6 of the carbon dioxide separation unit 20. More specifically, pure water stored in a liquid storage tank 28 is suctioned by a pump 32 and is allowed to pass through the ion-exchange resin 30 to obtain ion-exchange water, and the obtained ion-exchange water is supplied to the measurement water channel 6 of the carbon dioxide separation unit 20. The conductivity of the measurement water that has flowed through the measurement water channel 6 is measured by a conductivity meter 34 provided as the conductivity measuring unit 126. The conductivity is derived from carbon dioxide transferred from the intermediate water to the measurement water in the carbon dioxide separation unit 20. The measurement water that has passed through the conductivity meter 34 is returned to the liquid storage tank 28 and reused. The conductivity meter 34 may be integrated with the carbon dioxide separation unit 20 or may be provided separately from the carbon dioxide separation unit 20. In the latter case, the conductivity meter 34 is connected to the carbon dioxide separation unit 20 through a channel. The sample water that has flowed through the sample water channel 2 of the carbon dioxide separation unit 20 is discharged from the carbon dioxide separation unit 20.

As the intermediate water, pure water or deionized water is supplied to the intermediate water channel 4. Deionized water that has passed through the ion-exchange resin 30 can also be supplied as the intermediate water. The intermediate water and the sample water are in contact with each other with the sample water channel-side gas permeable membrane 8 being interposed therebetween, and the intermediate water and the measurement water are also in contact with each other with the measurement water channel-side gas permeable membrane 10 being interposed therebetween. The intermediate water that has flowed through the intermediate water channel 4 is discharged from the carbon dioxide separation unit 20.

Figure 3:
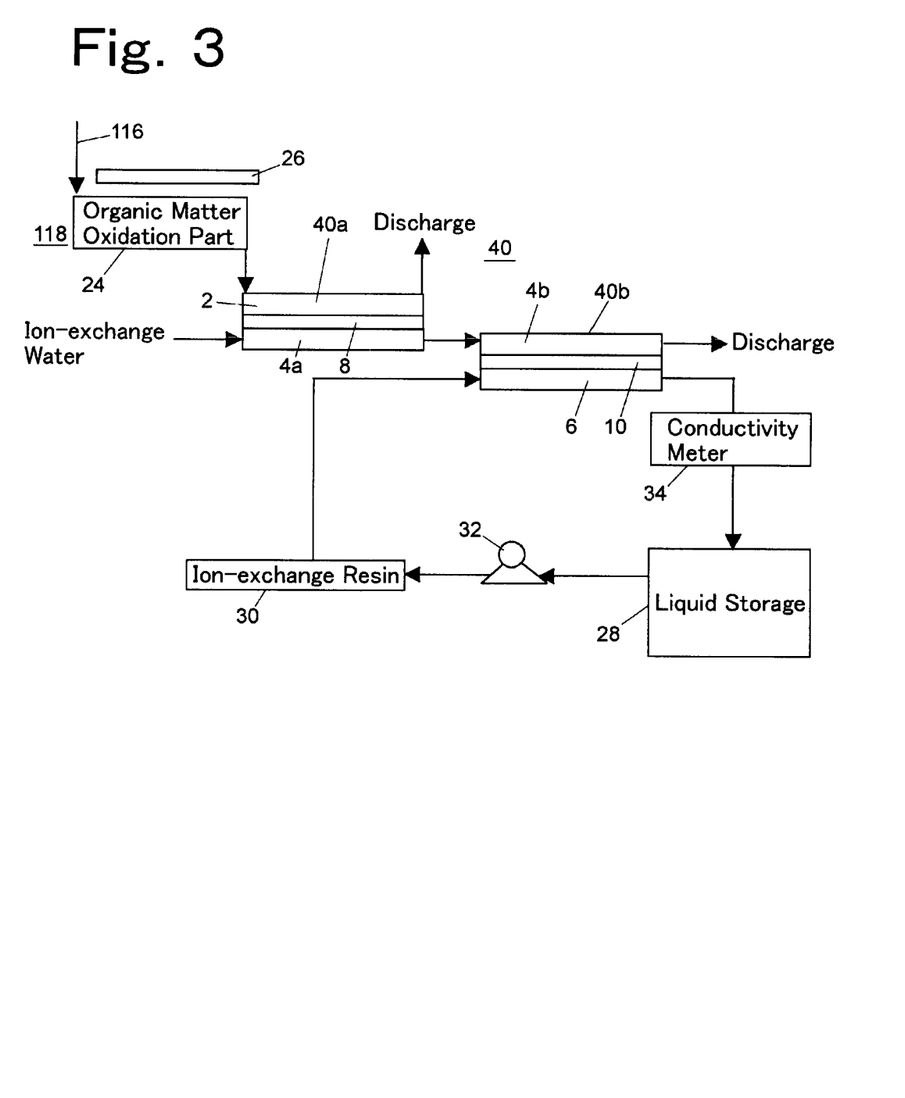
FIG. 3 is a block diagram showing a second embodiment of the oxidative decomposition unit, the carbon dioxide separation unit, and the conductivity measuring unit.

FIG. 3 shows another embodiment. As shown in FIG. 3, a carbon dioxide separation unit 40 that is another example of the carbon dioxide separation unit 124 is separated into a sample water-side gas exchange part 40a and a measurement water-side gas exchange part 40b. The intermediate water channel is separated into a sample water-side intermediate water channel 4a and a measurement water-side intermediate water channel 4b, and the channel 4a and the channel 4b are connected to each other through a connecting channel. The units other than the carbon dioxide separation unit 40 shown in FIG. 3 have the same structure as those shown in FIG. 2.

Figure 4:
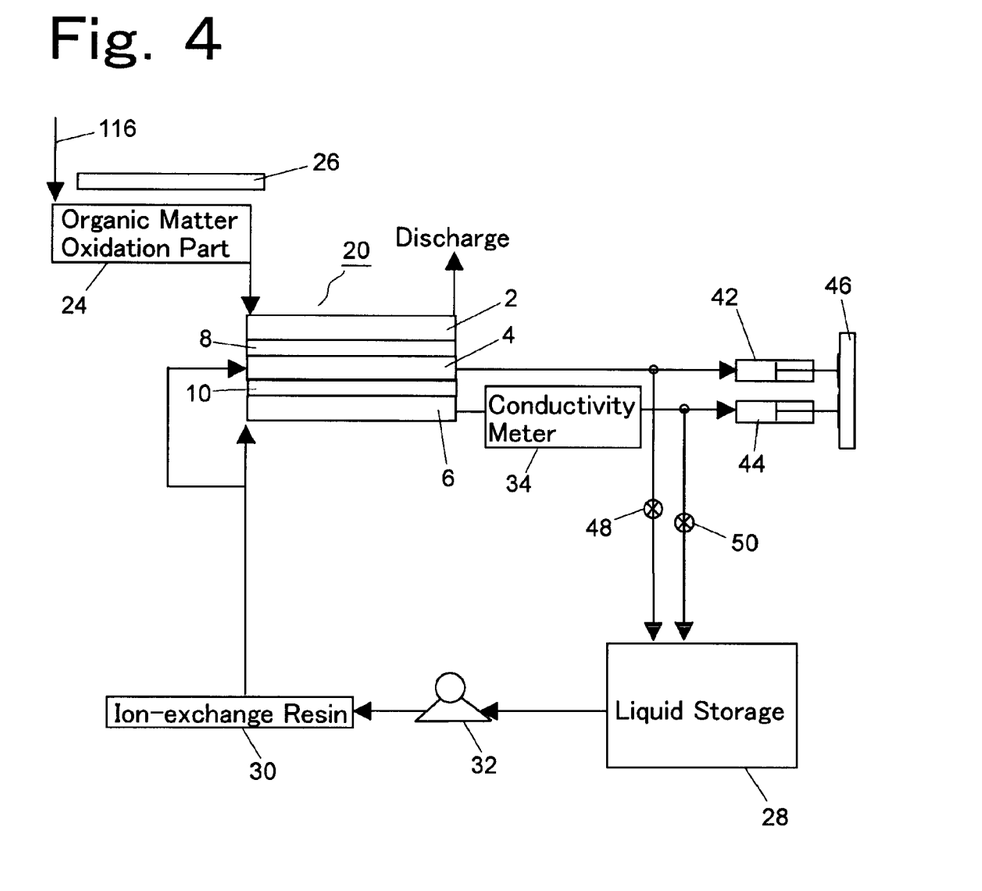
FIG. 4 is a block diagram showing a third embodiment of the oxidative decomposition unit, the carbon dioxide separation unit, and the conductivity measuring unit.

FIG. 4 shows yet another embodiment in which a common syringe pump is used to maintain a constant ratio between the flow rate of intermediate water and the flow rate of measurement water. The carbon dioxide separation unit 20 shown in FIG. 4 is the same as that according to the embodiment shown in FIG. 2, but may be separated into a sample water-side gas exchange part and a measurement water-side gas exchange part as shown in FIG. 3. As intermediate water and measurement water, the same ion-exchange water supplied by the pump 32 through the ion-exchange resin 30 is used. The measurement water is allowed to flow through the measurement water channel 6 to the conductivity meter 34. The intermediate water is allowed to flow through the intermediate water channel 4. A channel for returning the intermediate water to the liquid storage tank 28 is provided with a valve 48, and a channel for returning the measurement water to the liquid storage tank 28 is provided with a valve 50, and two syringes 42 and 44 of one syringe pump 46 are connected to these channels respectively to adjust the flow rates of the intermediate water and the measurement water. When the intermediate water and the measurement water are allowed to flow, the valves 48 and 50 are closed and the intermediate water and the measurement water are simultaneously suctioned into the syringes 42 and 44, respectively. Therefore, the intermediate water is allowed to flow at a flow rate determined by the inner diameter of the syringe 42, and the measurement water is allowed to flow at a flow rate determined by the inner diameter of the syringe 44. After the completion of measurement, the valves 48 and 50 are opened, and the intermediate water and the measurement water suctioned into the syringes 42 and 44 are ejected from the syringes 42 and 44 and returned to the liquid storage tank 28.

As described above, when the intermediate water discharged from the intermediate water channel 4 and the measurement water discharged from the measurement water channel 6 are simultaneously suctioned into the two syringes 42 and 44 fixed to the single syringe pump 46, the ratio between the flow rate of the intermediate water and the flow rate of the measurement water can be maintained at a predetermined constant value by selecting the diameters of the syringes 42 and 44. By maintaining a constant ratio between the flow rate of the intermediate water and the flow rate of the measurement water, it is possible to maintain a constant distribution ratio of a gas component from the intermediate water to the measurement water and therefore to achieve high measurement reproducibility.

Figure 5:
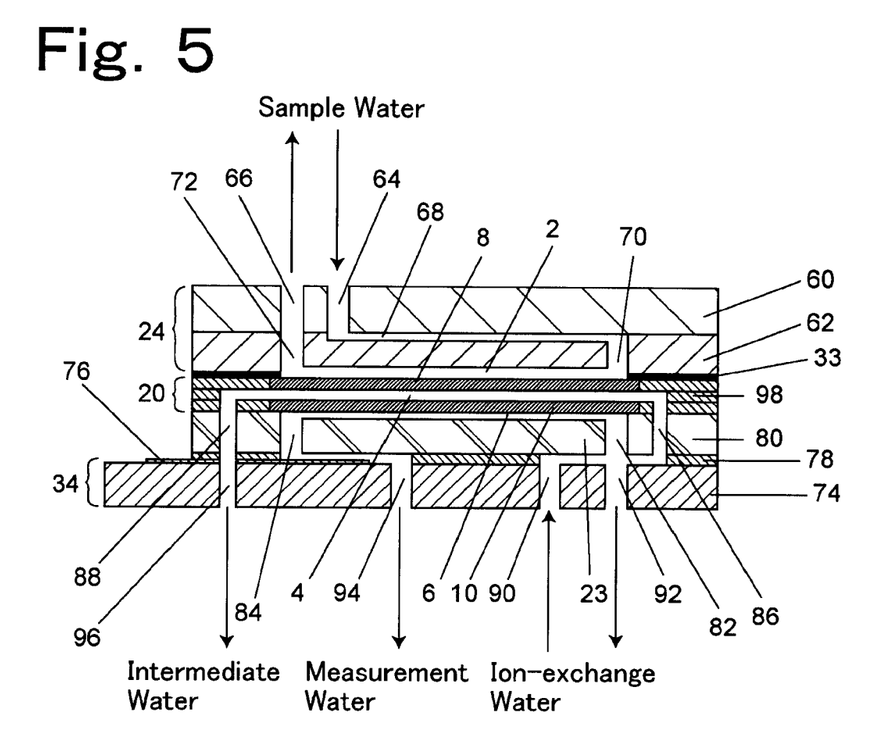
FIG. 5 is a block diagram showing a fourth embodiment of the oxidative decomposition unit, the carbon dioxide separation unit, and the conductivity measuring unit.

Hereinbelow, yet another embodiment in which the organic matter oxidation part 24, the carbon dioxide separation unit 20, and the conductivity meter 34 are integrated together will be described with reference to FIG. 5. It is to be noted that when it is necessary to differentiate between the front surface and the back surface of each substrate shown in FIG. 5, the upper surface and the lower surface thereof are referred to as "front surface" and "back surface" respectively.

The organic matter oxidation part 24 is constituted from a UV light-incident-side substrate 60 and a substrate 62 bonded to the substrate 60. The substrate 60 is formed from a UV light-permeable quartz substrate to decompose organic matter by ultraviolet light. Part of the substrate 60 is a UV light incident portion on which ultraviolet light is incident. The substrate 60 has a through hole 64 serving as a sample water inlet and a through hole 66 serving as a sample water outlet. The other substrate 62 is also formed from a quartz substrate. The substrate 62 has an oxidation part channel 68 formed in the front surface thereof, and one end of the oxidation part channel 68 is located at a position corresponding to the sample water inlet 64. Further, the substrate 62 has the sample water channel 2 formed in the back surface thereof, and one end of the sample water channel 2 is located at a position corresponding to the sample water outlet 66. The substrate 62 has a through hole 70 for connecting the other end of the oxidation part channel 68 and the other end of the sample water channel 2 together and a through hole 72 for connecting the one end of the sample water channel 2 and the sample water outlet 66 together. On the back surface of the substrate 62, that is, on the surface opposite to the surface of the substrate 62 bonded to the substrate 60, a light-blocking metal film 33 is provided to define a UV light-irradiated region. The light-blocking metal film 33 is, for example, a Pt/Ti film (a film obtained by forming a platinum film on a titanium film formed as a contact layer) having a thickness of 0.05 µm or more.

The size of each of the oxidation part channel 68 and the sample water channel 2 is not particularly limited, but the oxidation part channel 68 and the sample water channel 2 each have, for example, a width of about 1 mm, a depth of about 0.2 mm, and a length of about 200 mm, and can be formed by processing such as wet etching or dry etching. The through holes 64, 66, and 70 can be formed by, for example, sandblasting. The substrates 60 and 62 can be bonded together by hydrofluoric acid bonding.

The conductivity meter 34 is formed by bonding the back surface of a quartz substrate 80 onto an electrode pattern 76 formed by a Pt/Ti film on a quartz substrate 74 with a film 78, from which a channel portion has been cut out, being interposed therebetween.

Examples of the film 78 to be used include an adhesive fluorine resin film (e.g., NEOFLON (which is a trademark of Daikin Industries, Ltd.) EFEP having a thickness of 100 µm) and a PDMS (polydimethylsiloxane) film (e.g., SYLGARD® 184 having a thickness of 100 µm and manufactured by Dow Corning). On the electrode pattern 76, a channel through which measurement water flows is formed by the film 78.

The electrode pattern 76 can be formed by forming a Pt/Ti film by sputtering and subjecting the film to patterning by photolithography and etching used in semiconductor manufacturing processes or the field of micro processing. However, a method for forming the electrode pattern 76 is not particularly limited. The film for forming a channel on the electrode pattern 76 is not limited to a NEOFLON film or a PDMS film, and an adhesive organic film or an adhesive-coated thin film may be used.

In the front surface of the quartz substrate 80, the measurement water channel 6 is formed. The quartz substrate 80 has a measurement water branch channel 82 connected to one end of the measurement water channel 6 and a through hole 84 for connecting the other end of the measurement water channel 6 to the channel provided with the electrode pattern 76 of the conductivity meter 34. The quartz substrate 80 also has a through hole 86 serving as an intermediate water branch channel for introducing intermediate water and a through hole 88 serving as an intermediate water outlet for discharging intermediate water. The thickness of the quartz substrate 80 is not particularly limited, but is, for example, 1 mm.

The quartz substrate 74 has a through hole 90 serving as an ion-exchange water inlet for supplying ion-exchange water as deionized water and a through hole 92 serving as an ion-exchange water outlet for discharging excess ion-exchange water. The ion-exchange water inlet 90 is connected to the measurement water branch channel 82, the intermediate water branch channel 86, and the ion-exchange water outlet 92 through a channel formed by the PDMS film 78 sandwiched between the substrates 74 and 80.

The quartz substrate 74 also has a through hole 94 serving as a measurement water outlet for discharging measurement water from the channel provided with the electrode pattern 76 of the conductivity meter 34 after conductivity detection and a through hole 96 that is connected to the through hole 88 provided in the quartz substrate 80 to discharge intermediate water and serves as an intermediate water outlet for discharging intermediate water.

The back surface of the substrate 62 constituting the organic matter oxidation unit 24 and the front surface of the substrate 80 constituting a unit of the conductivity meter 34 are bonded together with the two gas permeable membranes 8 and 10 constituting the carbon dioxide separation unit being interposed therebetween. A PDMS film 98 is interposed between the gas permeable membranes 8 and 10 so that a gap is formed by the thickness of the PDMS film 98. Therefore, the intermediate water channel 4 is formed by patterning the PDMS film 98. The intermediate water channel 4 is configured so that one end of the intermediate water channel 4 is connected to the intermediate water branch channel 86 provided in the quartz substrate 80 to introduce intermediate water and the other end of the intermediate water channel 4 is connected to the through hole 88 for discharging intermediate water.

The gap between the gas permeable membranes 8 and 10 and the gap between the substrates 62 and 80 are sealed with film such as PDMS film so that the sample water channel 2 is formed between the gas permeable membrane 8 and the substrate 62 and the measurement water channel 6 is formed between the gas permeable membrane 10 and the substrate 80.

The gas permeable membranes 8 and 10 are not particularly limited, and membranes not having carbon dioxide selectivity are used. Examples of such gas permeable membranes 8 and 10 include porous fluorine resin membranes (e.g., POREFLON having a thickness of 30 μm and manufactured by Sumitomo Electric Industries, Ltd.).

According to this embodiment, sample water is introduced through the sample water inlet 64 of the substrate 60, flows through the oxidation part channel 68 and the sample water channel 2, and is discharged through the sample water outlet 66. During that time, the sample water is oxidized by the oxidation part 24 by UV irradiation, and is brought into contact with intermediate water with the gas permeable membrane 8 of the carbon dioxide separation unit 20 being interposed therebetween so that a gas component such as carbon dioxide is distributed to the intermediate water.

Ion-exchange water is produced outside this device and is introduced through the ion-exchange water inlet 90. Most of the introduced ion-exchange water is directly discharged through the ion-exchange water outlet 92, and only the needed amount of ion-exchange water is supplied to the measurement water channel 6 through the measurement water branch channel 82 and to the intermediate water channel 4 through the intermediate water branch channel 86.

The intermediate water channel 4 is in contact with both the gas permeable membrane 8 to be brought into contact with sample water and the gas permeable membrane 10 to be brought into contact with measurement water, and therefore, a gas component transferred from sample water to intermediate water is distributed to measurement water while reaching equilibrium with its ions, and then the intermediate water is discharged to the outside through the intermediate water outlets 88 and 96. The measurement water receives the gas component while flowing through the measurement water channel 6, passes through the conductivity meter 34, and is discharged through the measurement water outlet 94.

Hereinbelow, the results of measurement using the embodiment shown in FIGS. 1 and 2 will be described.

About 3 mL of pure water was collected as sample water in the syringe 106, and then phosphoric acid was added to adjust the pH of the pure water to about 4. Then, high-purity air was introduced into the syringe 106 at a flow rate of about 100 mL/min for 90 seconds, and then the pure water was sent to the organic matter oxidation part 24 of the oxidative decomposition unit 118. At this time, the oxidative decomposition function of the oxidative decomposition unit 118 was turned off by turning off the ultraviolet lamp 26 of the oxidative decomposition unit 118 or by blocking UV light with the shutter 27 provided in the oxidative decomposition unit 118 so that only the remaining $CO_2$ (inorganic carbon) in the pure water sample could be measured. The pure water sample that had passed through the oxidative decomposition unit 118 whose oxidative decomposition function was turned off was supplied to the carbon dioxide separation unit 118, and the conductivity of measurement water that had passed through the carbon dioxide separation unit 118 was measured by the conductivity measuring unit 126. In this way, a signal derived from $CO_2$ remaining in the pure water subjected to aeration treatment was detected and processed to obtain a system blank value.

The TOC of each of pure water and two potassium hydrogen phthalate standard solutions (500 μgC/L and 1000 μgC/L) was measured in a state where the oxidative decomposition function of the oxidative decomposition unit 118 was turned on. The TOC of each of these samples was measured five times.

The measurement results are shown in Table 1.

TABLE 1

| Signal values of samples | | | |
| --- | --- | --- | --- |
| System blank | Pure water | 500 ppb | 1000 ppb |
| 4.65 | 5.04 | 27.4 | 54.5 |
| 4.66 | 5.03 | 27.4 | 52.5 |
| 4.67 | 5.03 | 27.2 | 53.2 |
| 4.66 | 5.06 | 27.8 | 53.7 |
| 4.67 | 5.06 | 27.0 | 53.8 |
| 4.66 | 5.04 | 27.4 | 53.5 |

Figure 6:
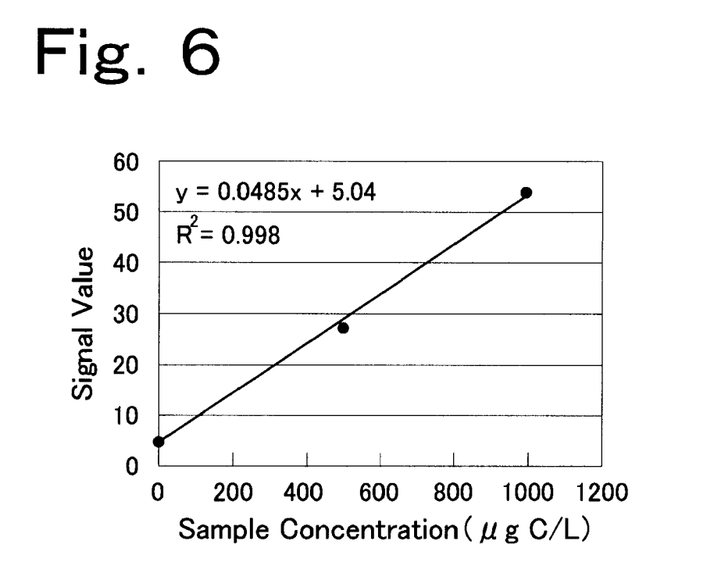
FIG. 6 is a graph showing a calibration curve.

FIG. 6 shows a calibration curve obtained from these measurement results. This calibration curve was prepared using averages of five TOC measurements shown in Table 1. The data of the calibration curve is held in the arithmetic section 132 of the arithmetic processing unit 128. The data of the calibration curve directly obtained from the measurement results shown in Table 1 is represented by the following formula: $y=0.0485x+5.04$, wherein y is a signal value and x is a sample concentration (TOC value).

The data of the calibration curve directly obtained from the measurement results is shifted so that its intercept value becomes the above system blank value to obtain the data of a corrected calibration curve. The data of the corrected calibration curve is represented by the following formula: $y=0.0485x+4.66$.

The TOC concentration of sample water can be determined from the corrected calibration curve and a measured value obtained by measuring the sample water in a state where the oxidative decomposition function of the oxidative decomposition unit 118 is turned on.

The TOC value of pure water can be estimated as follows using the system blank value and the calibration curve obtained using this embodiment:

TOC value=(signal value of pure water−system blank value)/$0.0485$=$(5.04-4.66)/0.0485$=$7.84$ μgC/L On the other hand, a TOC meter different from the TOC meter according to the present invention, that is, a TOC meter provided with a total carbon combustion unit for converting TOC contained in sample water into $CO_2$ gas using an oxidation catalyst to measure the $CO_2$ concentration in the gas phase was used to determine the TOC value of a pure water sample using a system blank value obtained by repeated cycles of oxidative decomposition and recovery of pure water that was the same as the pure water sample. As a result, the TOC value of the pure water sample was 6.6 μgC/L.

As described above, the TOC value of pure water determined by the TOC meter according to the embodiment of the present invention was 7.84 μgC/L, which was close to the TOC value of pure water determined using the conventional TOC meter. This indicates that the measurement of a system blank based on the system according to the present invention has high validity.

The invention claimed is:

1. A method for obtaining total organic carbon concentration of sample water using a total organic carbon measuring device comprising:

a sample supply unit that has a system for collecting and supplying sample water and subjecting the collected sample water to aeration treatment using a gas containing no carbon dioxide;

an oxidative decomposition unit that is connected to the sample supply unit, has oxidative decomposition function that oxidizes organic matter contained in the sample water supplied from the sample supply unit to carbon dioxide, and is capable of turning on and off the oxidative decomposition function;

a carbon dioxide separation unit that includes a sample water channel through which the sample water that has passed through the oxidative decomposition unit flows, a measurement water channel through which measurement water consisting of deionized water flows, and a gas permeable membrane interposed between the sample water channel and the measurement water channel to allow carbon dioxide to be transferred therethrough;

a conductivity measuring unit that measures a conductivity of the measurement water flowing from the carbon dioxide separation unit; and an arithmetic processing unit that includes a system blank holding section that holds, as a system blank value, a measured value obtained by the conductivity measuring unit when pure water collected in the sample supply unit and subjected to aeration treatment is allowed to pass through the oxidative decomposition unit of which oxidative decomposition function is turned off and then flows through the sample water channel, and an arithmetic section that calculates a total organic carbon concentration of the sample water from a system blank value held in the system blank holding section and a measured value obtained by the conductivity measuring unit when the sample water is allowed to pass through the oxidative decomposition unit of which oxidative decomposition function is turned on and then flows through the sample water channel;

the method comprising:

obtaining a system blank value by collecting pure water in the sample supply unit and subjecting the collected pure water to aeration treatment using a gas containing no carbon dioxide, turning the oxidative decomposition function of the oxidative decomposition unit off, passing the pure water through the oxidative decomposition unit of which the oxidative decomposition function is turned off, passing the pure water through the sample water channel of the carbon dioxide separation unit while passing measurement water through the measurement water channel to allow carbon dioxide to transfer between the pure water and the measurement water, and measuring the conductivity of the measurement water flowing from the carbon dioxide separation unit; and collecting sample water in the sample supply unit, turning the oxidative decomposition function of the oxidative decomposition unit on, passing the sample water through the oxidative decomposition unit of which the oxidative decomposition function is turned on, passing the sample water through the sample water channel of the carbon dioxide separation unit while passing measurement water through the measurement water channel to allow carbon dioxide to transfer between the sample water and the measurement water, and measuring the conductivity of the measurement water flowing from the carbon dioxide separation unit to obtain a measured value of the sample water;

calculating a total organic carbon concentration of the sample water from the system blank value and the measured value of the sample water, wherein the arithmetic processing unit holds calibration curve data representing a relationship between a measured value obtained by the conductivity measuring unit and a total organic carbon concentration of the sample water supplied from the sample supply unit, wherein the calibration curve data is corrected using the system blank value held in the system blank holding section to obtain corrected calibration curve data, and wherein the step of calculating a total organic carbon concentration of the sample water calculates the total organic carbon concentration from the corrected calibration curve data and the measured value of the sample water.

2. The method for obtaining total organic carbon concentration according to claim 1, wherein the corrected calibration curve data is obtained by shifting the calibration curve data obtained from a measured value so that its intercept value becomes a system blank value held in the system blank holding unit.

* * * * *